(12) United States Patent
Stanfield et al.

(10) Patent No.: US 9,063,054 B2
(45) Date of Patent: Jun. 23, 2015

(54) VITRO MEASUREMENT OF SUNSCREEN PROTECTION

(75) Inventors: Joseph W. Stanfield, Winston-Salem, NC (US); Joseph William Stanfield, III, Winston-Salem, NC (US)

(73) Assignee: Suncare Research Laboratories, LLC, Winston-Salem, NC (US)

( * ) Notice: Subject to any disclaimer, the term of this patent is extended or adjusted under 35 U.S.C. 154(b) by 52 days.

(21) Appl. No.: 14/004,173

(22) PCT Filed: Feb. 29, 2012

(86) PCT No.: PCT/US2012/027106
§ 371 (c)(1),
(2), (4) Date: Nov. 18, 2013

(87) PCT Pub. No.: WO2012/125292
PCT Pub. Date: Sep. 20, 2012

(65) Prior Publication Data
US 2014/0063504 A1    Mar. 6, 2014

Related U.S. Application Data

(60) Provisional application No. 61/451,632, filed on Mar. 11, 2011.

(51) Int. Cl.
G01N 21/00 (2006.01)
G01N 21/03 (2006.01)
G01N 21/33 (2006.01)
G01N 21/59 (2006.01)

(52) U.S. Cl.
CPC ............ G01N 21/03 (2013.01); G01N 21/0303 (2013.01); G01N 21/33 (2013.01); G01N 21/59 (2013.01)

(58) Field of Classification Search
USPC .................. 356/440, 432–436, 444; 250/373, 250/474.1; 424/59, 400; 623/15.11, 15.12; 602/43, 47, 52; 523/113
See application file for complete search history.

(56) References Cited

U.S. PATENT DOCUMENTS

| | | |
|---|---|---|
| 7,004,969 B2 | 2/2006 | Ishikubo et al. |
| 2002/0030986 A1 | 3/2002 | Egawa et al. |
| 2004/0219684 A1 | 11/2004 | Dueva-Koganov et al. |
| 2010/0014069 A1 | 1/2010 | Miura et al. |
| 2011/0020601 A1 | 1/2011 | Lutz et al. |

FOREIGN PATENT DOCUMENTS

| | | |
|---|---|---|
| EP | 1291640 | 3/2003 |
| EP | 2014974 | 1/2009 |

(Continued)

OTHER PUBLICATIONS

Diffey et al., "A New Substrate to Measure Sunscreen Protection Factors Throughout the Ultraviolet Spectrum," Journal of the Society of Cosmetic Chemists, vol. 40, No. 3, pp. 127-133, May/Jun. 1989.

(Continued)

*Primary Examiner* — Tri T Ton
(74) *Attorney, Agent, or Firm* — Womble Carlyle Sandridge & Rice; Carl B. Massey, Jr.; Bernard A. Brown, II

(57) ABSTRACT

Substrates and methods for in vitro determination of sunscreen protection factors (SPF) are disclosed.

17 Claims, 7 Drawing Sheets

(56) References Cited

FOREIGN PATENT DOCUMENTS

WO     WO-95/32390     11/1995
WO     WO-2008/113109     9/2008

OTHER PUBLICATIONS

Cole, "Sunscreen Protection in the Ultraviolet A Region: How to Measure the Effectiveness," Photodermatology, Photoimmunology & Photomedecine, vol. 17, Issue 1, pp. 2-10, Feb. 2001.

International Search Report for PCT/US2012/027106 dated Jun. 22, 2012.

Gers-Barlag et al., In Vitro Testing to Assess the UVA Protection Performance of Sun Care Products, International Journal of Cosmetic Science, vol. 23, No. 1, Mar. 1, 2001, pp. 3-14.

Springsteen et al., "In Vitro Measurement of Sun Protection Factor of Sunscreens by Diffuse Transmittance," vol. 380, Jan. 1, 1999, pp. 155-164.

Extended European Search Report mailed Jul. 10, 2014.

Top View

Side View  Indention

VITRO MEASUREMENT OF SUNSCREEN PROTECTION

TECHNICAL FIELD OF THE INVENTION

The invention relates to a substrate and to methods for in vitro sunscreen measurement. More particularly, the invention relates to a substrate approximating the distribution of sunscreen applied to human skin. The invention also relates to a method of using the substrate for measuring the absorbance or transmission properties of a sunscreen sample and methods for determining the integrated absorbance spectrum and sun protection value of a sunscreen sample.

BACKGROUND OF THE INVENTION

Sunscreens protect against sunburn by absorbing energy from sunlight before it reaches the skin. The degree of protection by a sunscreen is described by the sun protection factor (SPF). Typically, the SPF is measured in a laboratory on human volunteers by applying 2 mg/cm$^2$ of sunscreen to an area of the mid-back, allowing the sunscreen to dry for 15 minutes, then administering a series of 5 doses of ultraviolet radiation energy (UVR), simulating sunlight, to skin sites treated with the sunscreen. Another series of five UVR doses is applied within a skin area without the sunscreen. After 24 hours, the irradiated skin sites are examined to determine the SPF. The SPF is the lowest dose of UVR that caused mild sunburn in the sunscreen-treated area divided by the lowest dose of UVR that caused mild sunburn in the area without sunscreen. The label SPF of a sunscreen product is based on the average SPF for 20 volunteers. Label SPF values range from 2 to more than 100.

Because SPF measurement requires administration of UVR to humans, and UVR is a known carcinogen, it is desirable to replace the current in vivo method of measuring SPF with an in vitro method.

The goal of in vitro sunscreen measurement methods is to replace invasive tests on human volunteer subjects. Therefore, it is important to validate in vitro methods against a measurable in vivo benchmark, such as SPF, for a wide variety of formulations and protection factors. The basic measure of UV protection is the transmission spectrum, which yields absolute indices of protection, such as SPF and UVA protection factor. The logarithmic transformation of the transmission spectrum yields the absorbance spectra that are currently used for determination of ratios, such as UVA/UVB and UVA1/UV, the critical wavelength, and spectral uniformity index. See, e.g., Boots UK Limited, *Measurement of UVA: UVB ratio according to the Boots Star rating system* (2008); FDA, *Sunscreen Drug Products for Over-the-Counter Human Use: Proposed Amendment of Final Monograph Proposed Rule*, Federal Register, Vol. 72 165, 49070-49122 (2007); Diffey, *Int. J. Cosmet. Sci.* 16:47-52 (1994); and Diffey, *Int. J. Cosmet. Sci.*, 31:63-68 (2009). Changes in the absorbance spectrum that vary with applied UV doses also permit quantitative assessment of photostability of the sunscreen active ingredients.

In vitro measurement of sunscreen protection presents a significant challenge: the substrates used for SPF determination must adequately match skin surface parameters and measurement systems must provide an appropriate optical configuration and sufficient dynamic range and wavelength accuracy. An aspect is the use of measurement procedures and algorithms that permit evaluations of photolabile sunscreen products. Validation of in vitro SPF results against in vivo SPF results for photolabile sunscreen products requires measurements of transmission or absorbance spectra before irradiation and after several UV doses, chosen for consistency with the in vivo SPF. Likewise, in vitro measurement of the SPF for a photolabile sunscreen product with an unknown in vivo SPF requires an estimate of the SPF for selection of appropriate irradiation doses.

Estimated transmission or absorbance spectra and SPF may be determined using the in silico method, i.e. calculation of effective transmission or absorbance spectra using quantitative UV spectra of the UV absorbing ingredients available in databases obtained from UV spectroscopic measurements in dilute solutions, and taking filter concentrations in the respective sunscreen composition into account. For the simulation of realistic sunscreen film transmittance from filter composition and spectral data, the film irregularity profile must be considered, by applying a relevant mathematical film profile model. In addition, filter photoinstabilities can be accounted for in terms of the respective photodegradation constants, which are also available as experimentally determined databases. Herzog et al., *J. Pharm. Sci.* 93 (7):1780-1795 (2004). Thus, starting with available UV spectroscopic and photokinetic data, it is possible to simulate the dynamics of the absorbance spectra of sunscreen films of given filter compositions under irradiation, in a way that is very similar to the in vitro approach presented in Herzog et al. The in silico method may then be used to obtain the estimated SPF required to perform in vitro SPF measurements of photolabile sunscreen products with unknown in vivo SPF values.

Once in silico and in vitro methods are validated against in vivo SPF, based on laboratory solar simulators, it may be possible to determine absorbance spectra for determination of SPF, such as UVA/UVB and UVA1/UV, and the critical wavelength and spectral uniformity index that represent actual protection in sunlight. See, e.g., Boots UK Limited, Measurement of UVA:UVB ratio according to the Boots Star rating system (2008); FDA, *Sunscreen Drug Products for Over-the-Counter Human Use: Proposed Amendment of Final Monograph Proposed Rule*, Federal Register, Vol. 72 165, 49070-49122 (2007); Diffey, *Int. J. Cosmet. Sci.*, 16:47-52 (1994); and Diffey, *Int. J. Cosmet. Sci.*, 31: 63-68 (2009)).

Spectroradiometric instrumentation should possess sufficient dynamic range, signal-to-noise ratio, spatial response, speed of measurement, wavelength accuracy, and rejection of out-of-band radiation, to achieve the required measurements with sufficient accuracy. COLIPA, In vitro UV Protection Method Task Force, *In vitro method for the determination of the UVA protection factor and critical wavelength values of sunscreen products* (2009). UV doses required for absorbance measurements should not significantly change the properties of the sample.

An effective instrument would permit measurement of sample transmission with simultaneous irradiation using the same UV source. Miura et al., *Photochem. Photobiol. Sci.* 84:1569-1575 (2008). However, simultaneous irradiation and spectral measurements are currently difficult due to the relatively low irradiance levels in the short wavelength UVB range of simulated sunlight, and the relatively high UVB absorbance of sunscreens.

Miura et al. have described a UV transmission measurement system utilizing a highly sensitive UV photomultiplier tube that permits transmission measurements for sunscreens with SPF values exceeding 50. Miura et al., *Photochem. Photobiol.*, 84:1569-1575 (2008). See also U.S. Patent Application Publication Nos. 2010/0012850 A1 and 2010/0014069 A1 which disclose methods and instruments for evaluating UV radiation protection effects and which are hereby incorporated by reference in their entirety for such teachings.

The sample irradiation lamp should comply with the spectral and total irradiance requirements of the COLIPA in vitro UVA protection Method, in order to match the behavior of the sunscreen during in vivo SPF determination. COLIPA, In vitro UV Protection Method Task Force, *In vitro method for the determination of the UVA protection factor and critical wavelength values of sunscreen products* (2009). Finally, the substrate temperature range should be controlled to remain within the range of actual skin temperatures during UV irradiation.

Further, Tronnier et al. reported a method for irradiating sunscreens and measuring the transmitted erythemal effective UV dose using a detector with an erythemally-weighted response. Tronnier et al., *Perfumerie und Kosmetik* 77:326-329 (1996). The SPF was computed as the applied effective UV dose when the transmitted erythemal effective UV dose reached 1-minimal erythema dose (MED). Tronnier et al., *Perfumerie und Kosmetik* 77:326-329 (1996); Kockott et al., *Automatic in vitro evaluation of sun care products*. In: Proceedings of the 21$^{st}$ IFSCC Congress, Berlin (2000). This method has been extended by measuring the transmitted spectral irradiance at discrete time points using a spectroradiometer, and integrating the spectral irradiance values to compute the transmitted erythema, effective UV dose. Stanfield, *Cosmet. Sci.*, 52:412-413 (2001); Stanfield, In vitro techniques in sunscreen development. In: Shaath, *Sunscreens: Regulations and Commercial Development* (2005); and Stanfield, *SöFW J.* 132:19-22 (2006). A continuous least-squares power curve fit equation is utilized to permit computation of SPF and provide an index of photostability. The resulting UV Dose Response Model also provides the unique absorbance spectrum corresponding to the SPF (i.e., the Integrated Absorbance). The Integrated Absorbance Spectrum is appropriate for use in computing the ratios UVA/UVB and UVA1/UV, the critical wavelength and the spectral uniformity index that are consistent with absolute measures of protection. See Boots UK Limited, Measurement of UVA: UVB ratio according to the Boots Star rating system (2008); FDA, Sunscreen Drug Products for Over-the-Counter Human Use: Proposed Amendment of Final Monograph Proposed Rule, Federal Register, Vol. 72 165, 49070-49122 (2007); Diffey, *Int. J. Cosmet Sci.* 16:47-52 (1994); Diffey, *Int. J. Cosmet. Sci.* 31:63-68 (2009). Changes in the absorbance spectrum with applied UV doses permit assessment of photostability within spectral ranges corresponding to absorbance maxima of UV absorbing ingredients.

The SPF measured on human subjects typically serves as a benchmark for validating in vitro measurement results. The problem in validating in vitro measurements is selecting the appropriate in vitro SPF value to compare to the in vivo SPF. For example, the SPF of a photolabile sunscreen labeled as SPF 25 is substantially higher than 25, initially, and substantially lower than 25 after a UV dose of 25 MEDs.

A procedure for determining the SPF typically requires administration of four UV doses at intervals in MEDs of approximately 40%, 80%, 120%, and 160% of the expected SPF, ideally with the measured SPF in the middle of the range. An in silico estimate of the SPF can provide an initial estimate of the expected SPF. Measurements should be obtained from 5 to 10 sunscreen/substrate preparations. After the first set of measurements, the exposure range may be adjusted to focus the measurements on a revised expected SPF. See Stanfield, Osterwalder, & Herzog, *Photochem. Photobiol. Sci.* 9 489-494 (2010) which is incorporated herein by reference in its entirety for teaching methods to calculate the Integrated Absorbance Spectrum and SPF.

The unique absorbance spectrum that represents the SPF protection provided by a photolabile sunscreen during irradiation with a UV dose in MEDs corresponding to the SPF (Integrated Absorbance Spectrum) may be determined using a procedure analogous to that of the Dose Response SPF model. In the latter case, the ratio of the unweighted transmitted and applied UV doses is determined for each wavelength for time, $t_{MED}$, and used to compute a transmission spectrum that yields an absorbance spectrum. Stanfield, Osterwalder & Herzog, *Photochem. Photobiol. Sci.* 9:489-494 (2010).

The Integrated Absorbance Spectrum represents the performance of the sunscreen during irradiation with full-spectrum UV (290-400 nm). This is the appropriate absorbance spectrum for measuring spectral ratios that describe UVA protection, such as critical wavelength the Spectral Uniformity Index based on the SPF test using a laboratory solar simulator. Diffey, *Int. J. Cosmet. Sci.* 16:47(52) (1994); and Diffey, *Int. J. Cosmet. Sci.*, 31:63-68 (2009).

An additional hurdle is that, due to limitations on the duration of testing and total energy applied to the skin of human subjects, laboratory solar simulators do not simulate the solar spectra most frequently encountered by the world population, and tend to overestimate the actual SPF protection realized in sunlight. Seite et al., *Photodermatol. Photoimmunol. Photomed.* 22:67-77 (2006). Once in vitro methods are validated against benchmark in vivo SPF values, it may be possible to determine absorbance spectra using lamps that provide more accurate simulation of solar spectra. The Integrated Absorbance Spectrum measured with such a lamp may then be used for determination of ratios, such as UVA/UVB and UVA1/UV and the critical wavelength and spectral uniformity index that more accurately represent actual protection in sunlight. See Boots UK Limited, Measurement of UVA:UVB ratio according to the Boots Star rating system (2008); FDA, *Sunscreen Drug Products for Over-the-Counter Human Use: Proposed Amendment of Final Monograph Proposed Rule*, Federal Register, Vol. 72 165, 49070-49122 (2007); Diffey, *Int. J. Cosmet. Sci.*, 16:47-52 (1994); and Diffey, *Int. J. Cosmet. Sci.*, 31:63-68 (2009).

Importantly, for a given sunscreen formula, the absorbance spectrum depends not only on average film thickness, but also on the distribution of film thickness values, as demonstrated by Ferrero et al., *J. Cosmet Sci*, 54:463-481 (2003); and Herzog et al., *J Cosmet Sci.*, 53:11-26 (2002). Ideally, the substrate for in vitro measurements should resemble skin and its topography should simulate the film thickness distribution on skin, with application of 2 mg/cm$^2$ of sunscreen, as used for the in vivo SPF measurements that serve as benchmarks. Measured absorbance spectra and their dynamic behavior must simulate sunscreen behavior on skin.

In the development of Vitroskin®, Sottery provided a substrate composition and surface similar to those of skin, by incorporating protein, lipids, and salts, and simulating the hydration, pH, surface tension, and ionic strength of skin in order to model the surface interaction of sunscreens and skin. See FDC Reports, Inc., FDC Reports: "The Rose Sheet®" *Toiletries, Fragrances and Skin Care*, 14:44, 15 (1993). Vitroskin®, however does not replicate the thickness distribution of sunscreens on skin.

Other known substrates are a surgical tape labeled as Transpore™ (3M) and Mimskin® v.1.0 (The Australian Photobiology Testing Facility). Transpore™ lacks a topography that simulates skin, and is not compatible with many of the ingredients currently used in sunscreen products and Mimskin® is claimed to permit evaluation of UVA protection only.

In practice, the most commonly used substrates for in vitro measurements of sunscreens are PMMA plates that do not closely resemble skin, but are well characterized and commercially available with controlled roughness values from 2 to 16 µm. PMMA plates yield reasonable SPF estimates under a limited range of conditions. Ferrero et al. have evaluated the performance of substrates with various roughness values. Ferrero et al., *IFSCC Magazine* 9(2):97-108 (2006). Miura has reported results of a ring test comparing SPF results for substrates with 6 µm and 16 µm roughness values. The latter substrate was claimed to have a roughness value similar to that of skin and to permit application of 2 mg/cm$^2$ of sunscreen. Miura, *Comparison of high and low roughness substrates*. Presentation to ISO TC217 WG7. Baltimore, Jun. 22, 2009. However, the 16 µm roughness substrate has shown results similar to those of the HD-6 plate, with no significant advantage in accuracy.

International application WO 2008/113109 describes an artificial substrate made of two layers of polypropylene tape and a weighted mesh is forced onto the tape surface to emboss texture on the tape. The textured tape is then used as a SPF substrate. The foregoing substrate does not replicate the thickness profile of skin and has not yielded an advantage over other currently available substrates.

U.S. Patent Application Publication No. 2010/0075360 A1 describes the use of mouse fibroblast cells and human keratinocytes for measuring SPF values. The cells are irradiated with UV dosages and then quantitating cell death by viable staining. This method requires expensive and time-consuming preparation of cell monolayers and may suffer from reproducibility problems.

A useful substrate should not only replicate the thickness profile of skin, but also be transparent to UV, chemically and physically stable, resistant to solvents, non-fluorescing, and inexpensive.

COLIPA Guidelines and the ongoing development of ISO standards, have propagated an internationally accepted approach to in vitro measurements of sunscreen performance. See In vitro UV Protection Method Task Force, *In vitro method for the determination of the UVA protection factor and critical wavelength values of sunscreen products*, COLIPA (2009), which are hereby incorporated by reference for the teachings of the standard in vitro sunscreen performance measurements. These methods are applied not only to measurement of UVA protection factors and spectral ratio indexes of UVA protection for products with known SPF values, but also in efforts to measure SPF. Two PMMA substrates that have emerged in current guidelines and ongoing standard development: the Schönberg sandblasted 2 µm roughness plate (Schönberg Gmbh & Co KG, Hamburg, Germany) and the Helioscreen HD-6 molded plate with a 6 µm roughness (Helioscreen, Creil, France). The Helioscreen substrate is considered more representative of human skin. However, for a variety of reasons, in vitro SPF measurement of a representative sample of marketed sunscreen products has not been accomplished with consistently acceptable accuracy.

Some of the current challenges that the present invention addresses are: First, current substrates do not adequately address the complexity of the sunscreen film on skin. As shown in FIG. 1, when a sunscreen film is applied to human skin, the multiple thicknesses of the film are determined by skin topography, the forces exerted during product application and the properties of the sunscreen formulation. The resulting SPF depends on the overall UVR absorbance of the film. Because the SPF is exponentially related to the thickness of the sunscreen film, thin areas protect much less than thicker areas. The currently accepted substrate is a molded 5 cm×5 cm×3 mm polymethylmethacrylate (PMMA) plate designated as HD-6 (Helioscreen, Creil, France). Sunscreen samples are applied as prescribed in the International SPF Method: multiple droplets are deposited with a syringe/pipette, then spread over the plate with light pressure with a duration of 20 to 50 seconds. COLIPA, Cosmetic, Toiletries and Fragrances Association of South Africa, The European Cosmetic, Toiletry and Perfumery Association (COLIPA), Japan Cosmetics Industry Association (JCIA), International Sun Protection Factor (SPF) Test Method, May 2006, which are hereby incorporated by reference for the teachings of the standard in vitro SPF measurements. The sunscreen is applied at 1.3 mg/cm$^2$, then rubbed for approximately one minute using a bare finger, and incubated at 35° C. for 30 minutes before undergoing measurements of UVR transmission. To account for a potential lack of photostability, plate transmission is measured again after a specified UV dose, which was selected empirically based on analysis of the results of a multi-laboratory study.

The currently recommended application amount of sunscreen on HD-6 plates is only 1.3 mg/cm$^2$ demonstrating that this goal has not been met. Moreover, the measured roughness value of the HD-6 plate is 6 µm, while that of human skin is reported to be approximately 17 µm. Thus, the Helioscreen HD-6 substrates do not accurately replicate the topography of skin or sunscreen application on human skin. For example, when 2 mg/cm$^2$ of a sunscreen is applied to the skin, a significant amount of the sunscreen accumulates in the sulci (valleys) of the skin, leaving the plateaus (flat regions) protected by a much thinner layer. O'neill, *J. Pharmaceut. Sci.* 73:888-891 (1984). In order to replicate the actual thickness distribution of a sunscreen film applied to the skin at 2 mg/cm$^2$, the substrate must accommodate that amount of sunscreen.

Further, substrates for measuring SPF have been designed to reproduce the topography of skin, by sandblasting or by molding. The actual simulation of skin topography has been poor, and researchers have attempted to compensate using elaborate schemes in the product application procedure, such as rubbing for various lengths of time at various pressures. These measures have improved accuracy for particular formulas, but optimum application techniques often differ for different formulas.

Additionally, several widely used sunscreen ingredients are not photostable, which means that their ability to absorb UVR degrades as UVR is absorbed. The time course and extent of photodegradation depends on the thickness of the sunscreen film, therefore the substrate must simulate the film thickness distribution on skin, not only to duplicate the UVR absorbance on skin, but also to account for potential photodegradation.

In addition, the algorithm for measuring UVR transmission must account for photodegradation. The currently accepted method, using measurements before and after irradiation with a single dose of UVR, does not adequately account for photodegradation.

Finally, in silico methods for estimating SPF only consider the active agents of a sunscreen formula. Such methods account for lack of photostability, but do not account for aspects of the formula vehicle that improve the bonding to skin or the uniformity of the film. For example, a commercial product with a SPF of 85 returns an SPF of about 30 when the active ingredients are entered in the BASF Sunscreen Simulator. (See BASF Sunscreen Simulator online). Consequently, the simulation does not account for potential skin surface effects that may be important for the SPF measurement.

SUMMARY OF THE INVENTION

The invention relates to a substrate and to methods for in vitro sunscreen measurement.

One aspect of the present invention is a substrate for determining the absorbance or transmission of a substance comprising an optically transparent material comprising a defined height and comprising indentations comprising a plurality of separate or concentric shapes comprising progressively increasing depths (i.e., thicknesses), wherein the transmission of a substance can be measured at a plurality of thicknesses iteratively or simultaneously. In some aspects, the optically transparent material is quartz, optically clear glass, polymethylmethacrylate, polystyrene, silica, sapphire, ceramics, or a biological film or membrane. In some aspects, defined height is from about 0.5 mm to about 10 mm. In some aspects, the separate or concentric shapes are a circle, oval, square, or rectangle. In some aspects, the plurality of concentric shapes are a finite integer or a continuous distribution. In some aspects, the progressively increasing depths are stepped or continuous. In some aspects, the progressively increasing depths are from about 0.01 mm to 9.5 mm. In other aspects, the progressively increasing depths are from about 0.002 mm to 0.02 mm. In some aspects, the progressively increasing depth is stepped having at least twelve levels. In other aspects, the progressively increasing depth is stepped having at least three levels. In some aspects, the steps are sharp, beveled, or rounded. In some aspects, the indentations are smooth, textured, or roughened. In some aspects, the substance is sunscreen.

Another aspect of the present invention is a method for determining the absorbance or transmission of a substance, the method comprising (a) introducing a substance into the indentations of a substrate, the substrate comprising an optically transparent material comprising a defined height and comprising indentations comprising a plurality of separate or concentric shapes comprising progressively increasing depths (i.e., thicknesses), wherein the transmission of a substance can be measured at a plurality of thicknesses iteratively or simultaneously; (b) applying a continuous or intermittent (flashing) light source to the substance and substrate; and (c) measuring the time course of transmission or absorbance of the substance. In some aspects, the height of the substance is leveled by means of a leveler. In some aspects, the leveler comprises a plastic, rubber, or metal blade. In some aspects, the transmission or absorbance is measured using an integrating sphere, photomultiplier tube, sensor with an erythemally-weighted response, photo diode array, or charge coupled device (CCD). In some aspects, the continuous or intermittent (flashing) light source comprises a uniform beam. In some aspects, the integrated absorbance spectrum is determined for an unknown substance. In some aspects, the substance is sunscreen. In some aspects, the sunscreen is applied to the indentations using a syringe or a pipette. In some aspects, the indentations are filled with sunscreen. In some aspects, the sunscreen is spread throughout the indentations with light pressure for a duration of about 20 to about 50 seconds. In some aspects, the sunscreen is not spread throughout the indentations, but is leveled using a leveler.

Another aspect of the present invention is a method for determining the sun protection factor in vitro, the method comprising (a) introducing a sunscreen into the indentations of a substrate, the substrate comprising an optically transparent material comprising a defined height and comprising indentations comprising a plurality of separate or concentric shapes comprising progressively increasing depths (i.e., thicknesses), wherein the transmission of a substance can be measured at a plurality of thicknesses iteratively or simultaneously; (b) applying a continuous or intermittent (flashing) light source comprising a uniform beam to the sunscreen; (c) measuring the time course of transmission or absorbance of the sunscreen; (d) calculating the integrated absorbance spectrum; (e) analyzing the integrated absorbance spectrum; and (f) determining the sun protection factor. In some aspects, the sunscreen is applied to the indentations using a syringe or a pipette. In some aspects, the indentations are filled with sunscreen. In some aspects, the sunscreen is spread throughout the indentations with light pressure for a duration of about 20 to about 50 seconds. In some aspects, the sunscreen is not spread over the indentations.

BRIEF DESCRIPTION OF THE DRAWINGS

These and other features, aspects, and advantages of the present invention are better understood when the following Detailed Description is read with reference to the accompanying figures.

DETAILED DESCRIPTION OF THE INVENTION

Figure 1:
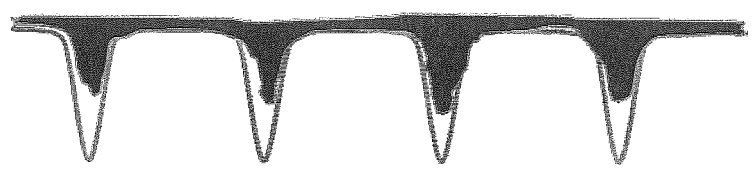
FIG. 1. Schematic cross-section of a sunscreen film on skin. When sunscreen is applied to human skin, a portion of the sunscreen enters the pores and thus covers these areas more thickly than other areas. The areas of skin that are sparsely covered are more susceptible to sunburn.

The present invention is a substrate for determining the absorbance or transmission of a sunscreen comprising an optically transparent material comprising a defined height and comprising indentations comprising a plurality of separate or concentric shapes comprising progressively increasing depths (i.e., thicknesses), wherein the transmission of a substance can be measured at a plurality of thicknesses iteratively or simultaneously. The optically transparent material can be quartz, optically clear glass, polymethylmethacrylate, polystyrene, silica, sapphire, ceramics, or a biological film or membrane. The defined height of the substrate is from about 0.5 mm to about 10 mm. The separate or concentric shapes in the substrate can be a circle, oval, square, or rectangle. The plurality of concentric shapes can be a finite integer or a continuous distribution. The progressively increasing depths can be stepped or continuous. The progressively increasing depths can be from about 0.01 mm to 9.5 mm. In other aspects, the progressively increasing depths can be from about 0.002 mm to 0.02 mm. The progressively increasing depth can be stepped and can have at least twelve levels. In other aspects, the progressively increasing depth is stepped has at least three levels. The step transitions can be sharp, beveled, or rounded. In some aspects, the indentations are smooth, textured, or roughened.

The present invention does not replicate the topography of skin, but replicates the sunscreen film thickness distribution, based on skin topography and the final thickness distribution of the sunscreen film on skin. This permits precise fabrication of the substrate and the reproducible application of finite amounts of sunscreen. The design of the substrate permits filling of the indentations by applying a sunscreen product over the entire surface with a controlled pressure, speed and duration, simulating application on skin, and then passing a blade across the surface to create a level upper surface of a film, reproducibly, with the desired thickness distribution. The sunscreen can be applied to the indentations using a syringe or a pipette. The sunscreen can also be spread throughout the indentations with light pressure for a duration of about 20 to about 50 seconds. In some cases, the indentations are filled with sunscreen, but the sunscreen is not spread throughout the indentations, but is leveled using a leveler.

Grouping the film thicknesses symmetrically within circular indentations in a plate provides the following advantages:
1. Replicates the film thickness distribution of a sunscreen on human skin.
2. Duplicates the sunscreen application amount used in the SPF test on human volunteers.
3. Enables precise fabrication of the required thickness distribution within the substrate well.
4. Permits filling of the indentations by applying a sunscreen product over the entire surface with a controlled pressure, speed, and duration, simulating application on skin.
5. Permits passing a blade across the substrate to create a reproducible, level upper surface of the sunscreen film.
6. Permits use of materials that provide accurate simulation of interactions of the sunscreen film with skin.
7. Permits spectroscopic measurements of UV transmission by the sunscreen using available instrumentation.

Another aspect of the present invention is a method for determining the absorbance or transmission of sunscreen. The method comprises introducing sunscreen into the indentations of a substrate. The substrate comprises an optically transparent material comprising a defined height and comprises indentations comprising a plurality of separate or concentric shapes comprising progressively increasing depths, wherein the transmission of a substance can be measured at a plurality of thicknesses iteratively or simultaneously. The sunscreen can be applied to the indentations using a syringe or a pipette. The sunscreen can also be spread throughout the indentations with light pressure for a duration of about 20 to about 50 seconds. In some cases, the indentations are filled with sunscreen, but the sunscreen is not spread throughout the indentations, but is leveled using a leveler. The height of the sunscreen in the substrate indentations are leveled by means of a leveler comprising a plastic, rubber, or metal blade. A continuous or intermittent (flashing) light source is applied to the sunscreen sample and the substrate and the time course of transmission or absorbance of the sunscreen is measured. In some aspects, the transmission or absorbance is measured using an integrating sphere, photomultiplier tube, sensor with an erythemally-weighted response, photo diode array, or charge coupled device (CCD). In most cases, the continuous or intermittent (flashing) light source comprises a uniform beam. In some aspects, the integrated absorbance spectrum and sun protection factor is determined for an unknown sunscreen.

Another aspect of the present invention is a method for determining the sun protection factor in vitro, the method comprising introducing a sunscreen into the indentations of a substrate, the substrate comprising an optically transparent material comprising a defined height and comprising indentations comprising a plurality of separate or concentric shapes comprising progressively increasing depths, wherein the transmission of a substance can be measured at a plurality of thicknesses iteratively or simultaneously; applying a continuous or intermittent (flashing) light source comprising a uniform beam to the sunscreen; measuring the time course of transmission or absorbance of the sunscreen; (d) calculating the integrated absorbance spectrum; analyzing the integrated absorbance spectrum; and determining the sun protection factor. As above, the sunscreen can be applied to the indentations using a syringe or a pipette. The sunscreen can also be spread throughout the indentations with light pressure for a duration of about 20 to about 50 seconds. In some cases, the indentations are filled with sunscreen, but the sunscreen is not spread throughout the indentations, but is leveled using a leveler. The height of the sunscreen in the substrate indentations is leveled by means of a leveler comprising a plastic, rubber, or metal blade.

EXAMPLES

The foregoing description of the embodiments, including preferred embodiments, of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the invention.

Example 1

Figure 2:
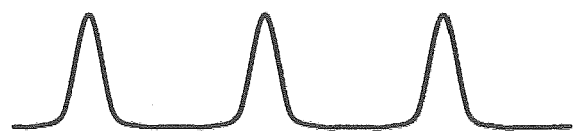
FIG. 2. Schematic thickness profile of a sunscreen on human skin. When the relative film thickness distribution of sunscreen applied to human skin are quantitated, the thickness profile is obtained. The "peak" regions reflect thick areas of sunscreen; the sides of the peaks represent intermediate thicknesses, and the interpeak regions (valleys) represent less thick areas of sunscreen.
Figure 3:
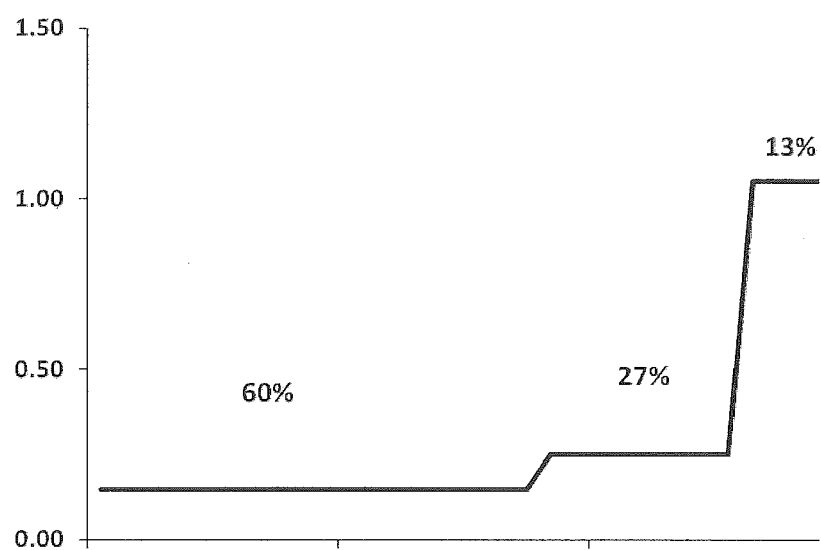
FIG. 3. Quantitative film thickness distribution of sunscreen within arbitrary ranges. When the relative film thickness distribution of sunscreen (shown in FIG. 2) are quantitated, approximately 60% of the sunscreen thickness is sparsely applied; 27% is intermediately applied; and 13% is thick or heavily applied. Accordingly, representing these distributions as depths in a substrate provides an accurate representation of typical sunscreen application on human skin.
Figure 4:
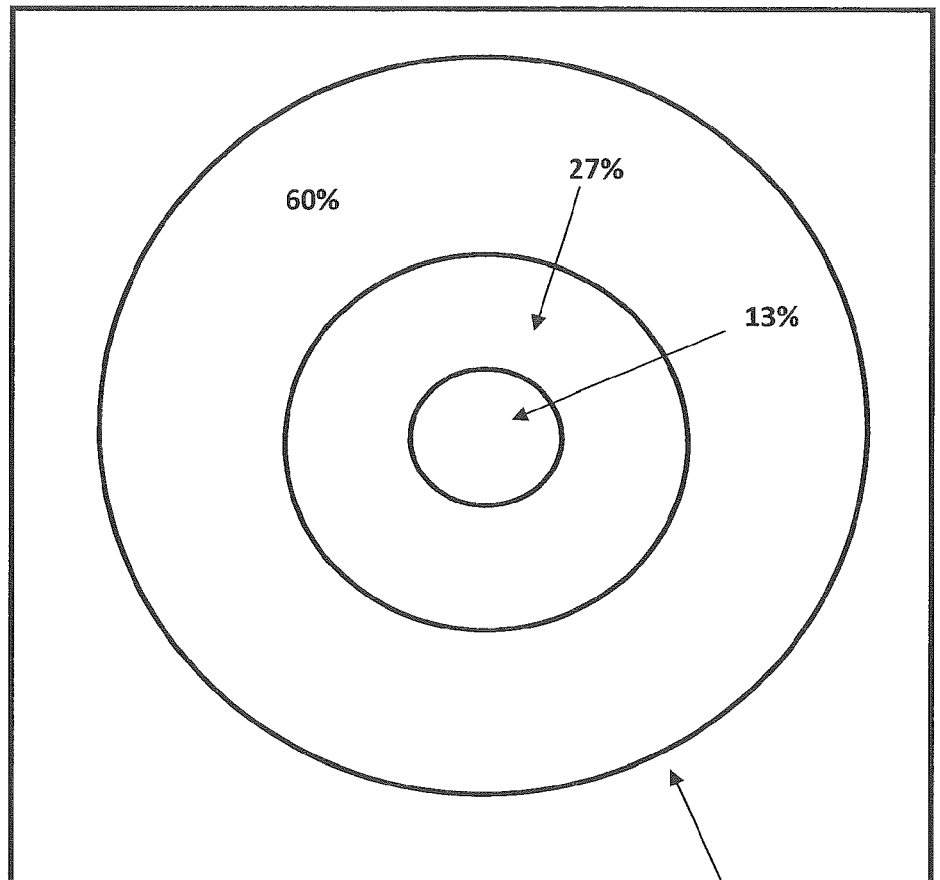
FIG. 4. Substrate permitting replication of sunscreen film thicknesses and sunscreen application amount on human skin. In this substrate, the 13%, 27%, and 60% coverage of sunscreen on human skin is represented by the different depth "steps" of the substrate. When the substrate and sample are illuminated with a continuous or intermittent (flashing) uniform beam, and the correct time course of absorbance or transmission is measured, then integrated absorbance spectrum can be obtained for different depths simultaneously.
Figure 4:
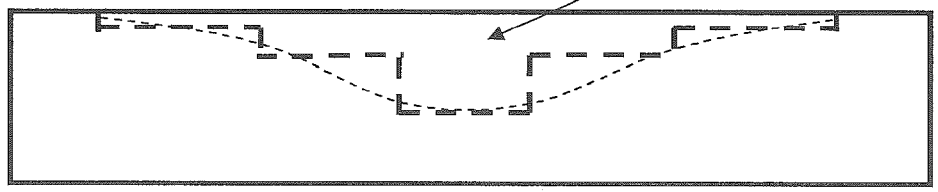

A schematic of a thickness profile of a sunscreen on human skin is shown in FIG. 2. The sunscreen film thicknesses may be grouped within defined ranges as illustrated in FIG. 3. Once a grouping of thicknesses within arbitrary ranges is achieved, a substrate may be designed that permits replication of sunscreen film thicknesses and their distribution on human skin, and the application amount of 2 mg/cm$^2$, as illustrated in FIG. 4. The area of substrate that contains the sunscreen is then irradiated continuously or intermittently with a uniform bean, and the applied and transmitted UVR doses are monitored to determine the UVR dose required for the film to transmit one MED. The value of the latter is the product SPF.

Figure 5:
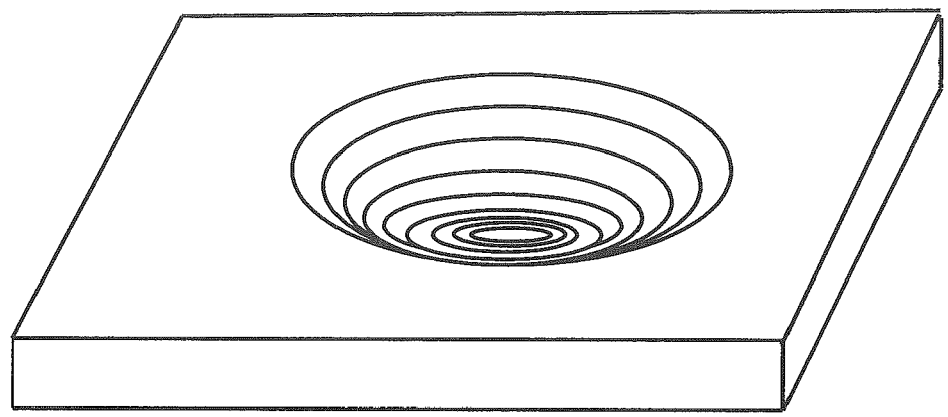
FIG. 5. Schematic of a substrate simulating the typical sunscreen film thickness distribution on skin. While successive concentric circular indentations are indicated in this schematic, oval, square, or rectangular depressions may also be useful.
Figure 6:
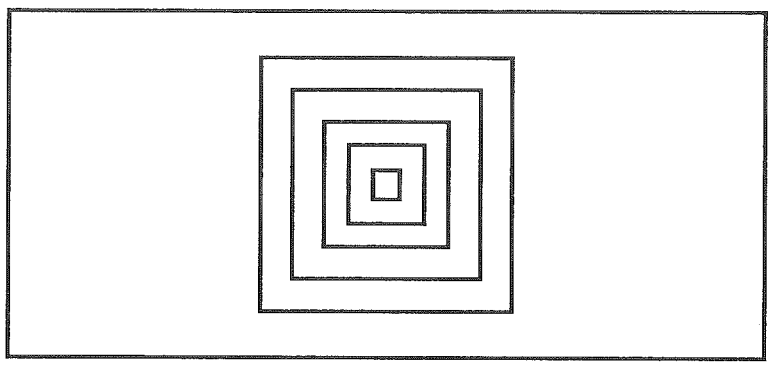
FIG. 6. Schematic of a substrate having square indentations simulating the typical sunscreen film thickness distribution on skin.
Figure 7:
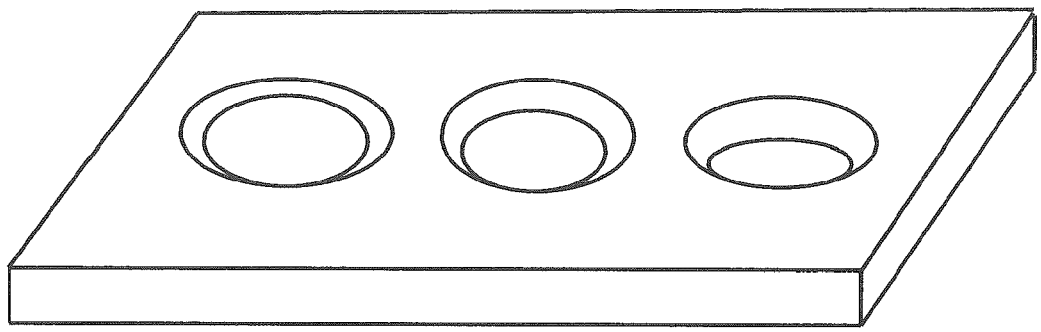
FIG. 7. Schematic of a substrate having individual indentations of differing depts. While circular indentations are indicated in this schematic, oval, square, or rectangular depressions may also be useful. In addition, while three indentations are indicated, this is exemplary and a plurality of indentations may be useful.

Two non-limiting representations of useful substrates are depicted in FIGS. 5-7. The substrate will be fabricated of adequately translucent materials such as quartz, PMMA, and biological films with properties that resemble skin. The latter should provide more accurate simulation of interactions of the sunscreen film with skin. The substrate can be manufactured via cast molding, computerized numerical control (CNC) milling, or any other method of manufacture.

What is claimed is:

1. A method for determining the absorbance or transmission of a sunscreen, the method comprising
   (a) applying a sunscreen to indentation(s) of a planar substrate, the substrate comprising an optically transparent material comprising a defined height and comprising on one surface:
      (i) an indentation comprising a plurality of concentric shapes so that the indentation has a progressively increasing depth; or
      (ii) a plurality of indentations comprising a plurality of separate shapes having progressively increasing depths;
      wherein the sunscreen applied to the indentation(s) fills the indentations;
   (b) applying a continuous or intermittent (flashing) light source to the sunscreen and substrate; and
   (c) measuring the time course of transmission or absorbance of the sunscreen.

2. The method of claim 1, wherein the transmission or absorbance is measured using an integrating sphere, photomultiplier tube, sensor with an erythemally-weighted response, photo diode array, or charge coupled device (CCD).

3. The method of claim 1, wherein the continuous or intermittent (flashing) light source comprises a uniform beam.

4. The method of claim 1, wherein the absorbance or transmission of the sunscreen is unknown.

5. The method of claim 1, wherein the sunscreen is applied to the indentations using a syringe or a pipette.

6. The method of claim 1, wherein the sunscreen is spread throughout the indentations with light pressure for a duration of about 20 to about 50 seconds.

7. The method of claim 1, wherein the sunscreen is leveled by means of a leveler.

8. The method of claim 7, wherein the leveler comprises a plastic, rubber, or metal blade.

9. The method of claim 1, wherein optically transparent material comprises quartz, optically clear glass, polymethylmethacrylate, polystyrene, silica, sapphire, ceramics, or a biological film or membrane.

10. The method of claim 1, wherein the defined height is from about 0.5 mm to about 10 mm.

11. The method of claim 1, wherein the shapes are a circle, oval, square, or rectangle.

12. The method of claim 1, wherein the progressively increasing depths are from about 0.01 mm to 9.5 mm.

13. The method of claim 1, wherein the progressively increasing depths are from about 0.002 mm to 0.02 mm.

14. The method of claim 1, wherein the progressively increasing depth is stepped having at least twelve levels.

15. The method of claim 1, wherein the progressively increasing depth is stepped having at least three levels.

16. The method of claim 1, wherein the indentations comprise smooth, textured, or roughened surfaces.

17. The method of claim 1, which is a method for determining the sun protection factor in vitro, the method comprising:
   (a) applying sunscreen into the indentation(s) of a substrate as used in claim 14;
   (b) applying a continuous or intermittent (flashing) light source comprising a uniform beam to the substrate and sunscreen;
   (c) measuring the time course of UV transmission or absorbance of sunscreen;
   (d) calculating the integrated absorbance spectrum;
   (e) analyzing the integrated absorbance spectrum; and
   (f) determining the sun protection factor.

* * * * *